United States Patent
Fischer et al.

(10) Patent No.: US 6,465,624 B1
(45) Date of Patent: Oct. 15, 2002

(54) PURIFICATION OF VON-WILLEBRAND FACTOR BY CATION EXCHANGER CHROMATOGRAPHY

(75) Inventors: Bernhard Fischer; Öyvind L. Schönberger, both of Vienna; Artur Mitterer, Mannsdorf; Christian Fiedler, Vienna; Friedrich Dorner, Vienna; Johann Eibl, Vienna, all of (AT)

(73) Assignee: Baxter Aktiengesellschaft, Vienna (AU)

( * ) Notice: Subject to any disclaimer, the term of this patent is extended or adjusted under 35 U.S.C. 154(b) by 0 days.

(21) Appl. No.: 09/367,460

(22) PCT Filed: Feb. 18, 1998

(86) PCT No.: PCT/AT98/00034

§ 371 (c)(1), (2), (4) Date: Oct. 21, 1999

(87) PCT Pub. No.: WO98/38219

PCT Pub. Date: Sep. 3, 1998

(30) Foreign Application Priority Data

Feb. 27, 1997 (AT) .................................................. 337/97

(51) Int. Cl.⁷ .................................................. A23J 1/00
(52) U.S. Cl. .................. 530/412; 530/413; 530/350; 530/300; 514/2; 514/21; 514/12; 260/112
(58) Field of Search ........................... 514/2, 21, 12; 530/350, 300, 412, 413; 260/112

(56) References Cited

U.S. PATENT DOCUMENTS

| | | | |
|---|---|---|---|
| 4,361,509 A | 11/1982 | Zimmerman et al. | |
| 5,006,642 A | 4/1991 | Newman et al. | |
| 5,252,709 A | 10/1993 | Burnouf et al. | 530/382 |
| 5,408,039 A | 4/1995 | Burnouf-Radosevich et al. | 530/383 |
| 5,789,153 A | 8/1998 | Falkner et al. | 435/5 |
| 5,858,658 A | 1/1999 | Haemmerle et al. | 435/6 |
| 5,869,617 A | 2/1999 | Fischer et al. | 530/381 |
| 5,872,099 A | 2/1999 | Fischer et al. | 514/12 |
| 5,876,969 A | 3/1999 | Fleer et al. | 435/69.7 |
| 5,880,265 A | 3/1999 | Fischer et al. | 530/383 |
| 5,887,152 A | 3/1999 | Fischer et al. | 514/12 |
| 5,892,005 A | 4/1999 | Fischer et al. | 530/413 |
| 6,103,693 A | 8/2000 | Fischer et al. | 514/12 |

FOREIGN PATENT DOCUMENTS

| | | | |
|---|---|---|---|
| CA | 2009946 | 4/2000 | C07K/14/745 |
| DE | 4435485 | 3/1996 | |
| EP | 0 469 985 A1 | 8/1991 | |
| EP | 0 503 991 A1 | 2/1992 | |
| EP | 0 600 480 A2 | 12/1993 | |
| EP | 0 383 234 B1 | 11/1994 | C07K/3/22 |
| WO | WO 89/12065 | 12/1989 | |
| WO | WO 91/13093 | 9/1991 | |
| WO | WO 93/15199 | 8/1993 | |
| WO | WO 96/10584 | 4/1996 | |

OTHER PUBLICATIONS

International Search Report for PCT/AT98/00034, dated Jun. 16, 1998.

Bradford, M.M., "A Rapid and Sensitive Method for the Quantitation of Microgram Quantities of Protein Using the Principle of Protein–Dye Binding" *Analytical Biochem.* 72, 1976, pp. 248–254.

Josic, D.J. et al., "Purification of Factor VIII and von Willebrand Factor From Human Plasma By Anion–Exchange Chromatography", *Chem. Abs.*, vol. 122, 1995, p. 502.

Dazey, B. et al., "Chromatography in Process for Manufacturing von Willebrand Factor Having a Very High Purity", *Chem. Abs.*, vol. 116, 1992, p. 454.

Burnouf–Radosevich, M. et al., "Chromatographic Preparation of a Therapeutic Highly Purified von Willebrand Factor Concentrate From Human Cryoprecipitate", *Chem. Abs.*, vol. 116, 1992, p. 446.

Saundry, R.H. et al., "Chromatography of vWF on Dextran Sulfate Sepharose", *Chem. Abs.*, vol. 108, 1988, p. 297.

Official Action for A 337/97 dated Aug. 27, 1997 (translation).

Primary Examiner—Karen Cochrane Carlson
Assistant Examiner—Hope A. Robinson
(74) Attorney, Agent, or Firm—Townsend and Townsend and Crew LLP (57) ABSTRACT

Disclosed are a method of recovering vWF in which vWF at a low salt concentration is bound to a cation exchanger and vWF having a high specific activity is recovered by fractionated elution, as well as a preparation having purified vWF obtainable by this method.

22 Claims, 3 Drawing Sheets

PURIFICATION OF VON-WILLEBRAND FACTOR BY CATION EXCHANGER CHROMATOGRAPHY

CROSS-REFERENCE TO RELATED APPLICATIONS

This application is the U.S. national phase of PCT/AT98/00034 filed Feb. 18, 1998, which claims priority from the Austrian application A 337/7 filed Feb. 27, 1997.

FIELD OF THE INVENTION

The invention relates to a method of recovering a purified von Willebrand factor (vWF) by means of cation exchange chromatography.

BACKGROUND

In plasma, vWF circulates at a concentration of from 5–10 mg/l, partly in the form of a non-covalent complex with factor VIII. vWF is a glycoprotein which is formed in various cells of the human body and later is liberated into the circulation. At this, a vWF dimer (primary vWF dimer) having a molecular weight of approximately 450000 Da is synthesized in the cells, starting from a polypeptide chain having a molecular weight of approximately 225000 Da (vWF monomer) by forming several sulfur bonds. From the vWF dimers, further polymers of vWF with ever increasing molecular weights, up to approximately 20000000 Da, are in turn formed by forming links via sulfur bonds.

One important criterion for characterizing vWF is the multimer-structure analysis by agarose electrophoresis. It is assumed that particularly the high-molecular vWF polymers are of essential importance in the coagulation of blood. The functional activity of vWF usually is determined by the ristocetin-cofactor-activity (vWF:RistCoF). The ratio between activity and vWF antigen concentration (vWF:Ag) is determined as a characteristic for the purity and specific efficacy of vWF. The specific activity of a preparation increases with an increasing ratio of vWF:RistCoF to vWF:Ag.

vWF assumes an important function within hemostasis. It circulates in plasma partly as a complex with factor VIII. which aids the coagulation of blood as a cofactor. Factor VIII is stabilized by complex formation with vWF and protected from proteolytic degradation thereby. A further object of vWF is its participation in thrombocyte aggregation which makes an important contribution to primary hemostasis. At this, vWF binds to the glycoproteins Ib and IIb/IIIa of the surface receptors of the thrombocytes and thus cross-links the thrombocytes to a thrombocyte aggregate. What is furthermore important for primary hemostasis is the affinity of vWF to collagen, a component of the extracellular matrix which, in intact vessels, does not have a direct contact with blood, since it is shielded from the blood flow by a monolayer of endothelial cells. When blood vessels are injured, a local detachment of the endothelial cell layer occurs at the site of lesion, resulting in a direct exposure of the components of the extracellular matrix to the blood. By its affinity to collagen, vWF is capable of fixing the forming thrombocyte aggregate in the damaged vessel region to the exposed subendothelium. This results in a first, labile wound closure which will be further strengthened by the subsequent blood coagulation.

von Willebrand syndrome is characterized by a deficiency of a functional von Willebrand factor or by an abnormal spectrum in the multimer composition of the von Willebrand factor. On account of a deficient stabilization of factor VIII, patients afflicted with von Willebrand syndrome may develop a factor VIII deficiency in spite of the fact that usually the synthesis rate of factor VIII is normal, such factor VIII deficiency being a consequence of the greatly reduced plasma half-life of this coagulation factor. Therefore, patients suffering from von Willebrand syndrome may exhibit symptoms similar to those of hemophilia A patients (phenotypic hemophilia). The lack of functionally active vWF may also cause dysfunctions of thrombocyte aggregation and adhesion in patients afflicted with von Willebrand syndrome, which may lead to defects in primary hemostasis. On account of dysfunctions of these vWF-mediated procedures, patients afflicted with von Willebrand syndrome exhibit increased bleeding times.

For the treatment of von Willebrand syndrome, thus vWF preparations must be administered which balance out the lack of functionally active vWF. To this end, preparations may be used which are also used in the therapy of hemophilia A, such as cryoprecipitate or the factor VIII concentrates prepared therefrom, which contain complexes of factor VIII and vWF. However, for the treatment of hemophilia A, better purified factor VIII:C concentrates are always used which either do not contain vWF or contain merely traces thereof. Since supplementing patients afflicted with von Willebrand syndrome with factor VIII is not necessary, and since the factor VIII application harbours the risk of inducing inhibitory factor VIII antibodies in the patient, a vWF preparation as free as possible from contaminating factor VIII would be very desirable for the treatment of von Willebrand syndrome. Therefore, there is a demand for pure and virus-safe von Willebrand factor preparations having a high specific activity.

In the literature, various methods of purifying and recovering vWF have been disclosed.

EP 0 503 991 describes the purification of vWF from human cryoprecipitate by three successive chromatographic steps: 1) anion exchange chromatography on TSK-DEAE Fractogel, and elution of vWF by means of 0.15 M NaCl; 2) another anion exchange chromatography on TSK-DEAE Fractogel, and elution of vWF by means of 0.17 M NaCl; and 3) affinity chromatography on gelatin sepharose to separate the contaminating fibrinogen. There, amino acid- and calcium ion-containing buffers were used.

WO 89/12065 describes the separation of plasmatic vWF from factor VIII and further proteins by binding the proteins to an anion exchanger and step-wise elution by increasing the salt concentration. The vWF-containing fraction was chromatographed for a second time via an anion exchanger and recovered as a concentrate.

EP 0 469 985 discloses the purification of plasmatic vWF from cryoprecipitate, wherein factor VIII is selectively bound to an anion exchanger in a first step at a salt concentration of 250 mM, while vWF remains in the supernatant. After lowering the salt concentration of the vWF-containing supernatant to a salt concentration of between 100 mM and 150 mM, vWF is bound to a second anion exchanger and eluted at pH 6.6 with 300–350 mM NaCl. There, vWF having an activity of at least 50 U/mg is recovered, which contains a portion of factor VIII of <2%.

DE 39 04 354 describes the recovery of plasmatic vWF from cryoprecipitate, and the separation of vWF from factor VIII by selective adsorption of factor VIII on an anion exchanger, while vWF remains in solution. There, a solution containing 160 U/ml of vWF is recovered.

U.S. Pat. No. 5,006,642 describes the recovery of vWF from a solution of vWF and chaotropic agent, incurred as a by-product according to U.S. Pat. No. 4,361,509, by dialysis against a suitable buffer or by desalting the solution by means of a further chromatographic step.

EP 0 383 234 describes the production of a vWF concentrate by means of anion exchange chromatography, wherein a factor VIII/vWF-complex contained in a solution is dissociated by the addition of a calcium and amino-acid-containing buffer, and a vWF concentrate is recovered.

WO 96/10584 describes a method of recovering highly purified recombinant vWF by means of combined anion exchange/heparin affinity chromatography, and EP 0 705 846 describes the separation of high and low molecular fractions of recombinant vWF by means of heparin affinity chromatography.

To recover a purified vWF preparation having high specific activity, it has been necessary so far to combine several chromatographic steps. In particular, the production of preparations particularly containing high-molecular vWF multimers has so far been possible only via a heparin affinity chromatography. Heparin, however, is a relatively expensive chromatographic material.

SUMMARY

It is the object of the present invention to provide a method of recovering purified vWF having an improved specific activity, which method is suitable for a large technical application on an industrial scale. The method should be usable for the purification of both recombinant and plasmatic vWF.

According to the invention, this object is achieved in that a method of recovering vWF is provided, in which vWF at a low salt concentration is bound to a cation exchanger, and vWF consisting particularly of high-molecular vWF multimers having a high specific activity, is recovered by step-wise fractionated elution. The recovery and enrichment of vWF having an improved activity and stability is particularly effected in that by increasing the salt concentration step-wise, at first fractions containing low-molecular vWF multimers, inactive degradation products and unspecific accompanying proteins are separated at a medium salt concentration, and fractions containing high-molecular vWF multimers having a high specific activity are recovered at a higher salt concentration.

On account of its acidic isoelectric point (IEP=5.5 to 6) and its negative net charge resulting therefrom, vWF usually is purified in a weakly acidic to basic environment via positively charged anion exchangers. Thus, on account of the methods of purifying vWF by means of positively charged anion exchangers described so far, vWF, at a pH lying above the IEP of vWF and at a low salt concentration, could not be expected to bind to a negatively charged gel matrix of a cation exchanger and to be selectively elutable therefrom by raising the salt concentration. Neither could it be expected that by a step-wise elution at a salt concentration of ≧300 mM, vWF consisting particularly of high-molecular vWF multimers would be obtained.

It has been found within the scope of the present invention that with the method according to the invention, departing from an impure biological material, purified fractions are obtained which are substantially free from contaminating nucleic acids. Thereby, in addition to the unspecific accompanying proteins, also nucleic acids are removed from protein preparations by this method. This effect cannot be performed with conventional methods by means of anion exchangers, since nucleic acids, on account of their negative charge, bind to the anion exchanger, detach from the anion exchanger again by increasing the salt conqgntration, and get into the eluate.

DETAILED DESCRIPTION OF THE INVENTION

When purifying vWF, particular attention must be paid that, on account of the size of vWF ranging from 500 000 to several millions, only such carrier-materials which do not impede the diffusion and distribution of the vWF molecule in the carrier materials used will result in good purification and good yields. When carrying out the method according to the invention of purifying vWF having a high specific activity by means of cation exchanger, a gel matrix is used which has not only a high loading capacity, is robust to handle and has a clear elution profile, but which also can be used economically on an industrial scale. Thus, the method according to the invention is particularly interesting for the recovery of purified vWF on a large technical scale.

Every known cation exchanger can be used for carrying out this method, cation exchangers having a sulfopropyl- or carboxymethyl-group conjugated carrier being preferred. SP-Sepharose® Fast Flow and CM-Sepharose® Fast Flow (Pharmacia), Fractogel® EMD-SO3 and Fractogel® EMD COOH (Merck), Poros® 10 SP and Poros® 10S (Perseptive Biosystems) and Toyopearl™ SP 550 C and Toyopearl™ CM-650 (M) (TosoHaas) have, e.g., proved to be well suitable.

A large-porous gel having tentacle structure of the type of Fractogel® EMD-SO3 and Fractogel® EMD COOH (Merck) has proved particularly suitable for the recovery of purified vWF.

The adsorption of vWF on the cation exchanger is preferably effected at a salt concentration in the buffer of ≦250 mM. Preferred adsorption buffers thus have a salt concentration of from 50 to 250 mM, in particular in the range of 150 mM–250 mM (e.g. 150 mM). By a step-wise raising of the salt concentration in the buffer, vWF substantially consisting of high-molecular vWF multimers can be eluted selectively at a salt concentration of ≧300 mM. Low-molecular vWF multimers and proteolytic vWF degradation products which are contained in the vWF-containing solution and which have a low specific activity in terms of vWF activity, in particular in terms of ristocetin-cofactor activity, which have a collagen binding activity and which have a specific platelet agglutination activity, are eluted from the cation exchanger at a salt concentration of between ≧250 mM and ≦300 mM, preferably at 300 mM, and separated.

Adsorption and desorption of vWF may be effected in a buffer containing a mono- or bivalent metal ion as salt, NaCl being preferably used as the salt.

In the method according to the invention, as the buffer system for eluting the proteins bound to the cation exchanger, preferably a buffer solution comprised of buffer substances, in particular glycine, phosphate buffer or citrated buffer, and salt are used. There, the buffer used preferably does not contain any Ca ions.

The elution buffer may have a pH ranging between 5.0 and 8.5, preferably between 6.0 and 8.0.

The method according to the invention may be carried out as a batch method or as a column chromatography.

The optimal parameters, such as salt concentration, pH and temperature, for carrying out the method according to the invention are, however, each dependent on the cation exchanger material used. Optimization of the conditions disclosed within the scope of the present invention for carrying out the method for each individually used cation exchanger type is, however, within the general knowledge of a skilled artisan.

In particular, by means of the method according to the invention a vWF is recovered and enriched, which particularly consists of high-molecular vWF multimers. Low-molecular vWF multimers and vWF fragments having a low specific platelet agglutinating activity are separated selectively, so that fractions particularly containing high-molecular vWF multimers having a high activity and specificity are obtained.

The recovered vWF fraction(s) is (are) substantially free from low-molecular vWF multimers, vWF fragments with a low specific activity, factor VIII complex, factor VIII:C, non-specific accompanying proteins and contaminating nucleic acids.

Any vWF-containing solution may be used as the starting material for recovering purified vWF by means of the method according to the invention. Starting materials are in particular biological materials, such as plasma, a plasma fraction, cryoprecipitate or a supernatant or an extract of a recombinant cell culture.

vWF-containing solutions may, however, also be enriched protein solutions which have been pre-purified by a preceding purification step, e.g. via gel filtration, anion exchange chromatography, affinity chromatography or a combination thereof. By these preceding procedures it is particularly achieved that vWF is enriched and non-specific accompanying proteins, in particular factor VIII or factor VIII-complex, are selectively separated.

According to a particular embodiment of the method of the invention, a vWF-containing fraction enriched via an anion exchanger is used as the starting solution.

By means of anion exchange chromatography, vWF may, depending on the manner of carrying out the anion exchange chromatography, either pass the anion exchanger freely as a non-bound material, or it may adsorb thereto. Thus, e.g., vWF is recovered from a plasma fraction and enriched in that both vWF and factor VIII/vWF-complex bind to an anion exchanger at a low ionic strength and salt concentration in a weakly acidic environment. vWF is then selectively eluted from the anion exchanger at a medium salt concentration of from 150 mM to 250 mM, while factor VIII-complex and free-non-complexed factor VIII desorb only at a high salt concentration of >300 mM.

An enriched vWF fraction can also be obtained in that a vWF-containing solution at a medium salt concentration between 100 mM and 200 mM is treated with an anion exchanger, wherein factor VIII-complex binds to the anion exchanger, while vWF remains in solution. Bound factor VIII-complex may subsequently be recovered from the anion exchanger by increasing the salt concentration.

According to a particular embodiment, vWF present in an enriched solution with a salt concentration of $\leq 250$ mM is recovered directly from the effluent or eluate or is recovered as the supernatant, respectively (in the batch method) and, optionally is bound to the cation exchanger without changing the ionic strength or the salt concentration. The salt concentration may, however, be lowered by diluting, if necessary.

This embodiment has the particular advantage that a simple combination of anion/cation exchange chromatography is possible, without requiring complex re-buffering, dialysis or the like of the enriched proteins.

Thus, an enriched vWF-containing fraction can be obtained by a first chromatographic step, and a purification and separation of high-molecular and low-molecular vWF fractions can be achieved by a subsequent cation exchange chromatography. Yet also other combinations, such as, e.g., affinity/cation exchange chromatography, anion exchange/affinity/cation exchange chromatography are possible to attain a further enrichment and a selective recovery of vWF having a high specific activity.

By means of the above-described method according to the invention, vWF having a high specific activity is at least 80fold enriched from an impure vWF-containing material.

Since, in principle, any biological material may be contaminated with infectious pathogens, the vWF-containing fraction obtained is treated for an inactivation or depletion of viruses so as to produce a virus-safe preparation. To this end, all the methods known from the prior art, such as chemical/physical methods, inactivation by combination of a photoactive substance and light, or depletion by filtration may be used. In particular, a heat treatment in solution or in the solid state, respectively, which reliably can inactivate both lipid-enveloped and non-lipid-enveloped viruses is suitable for an inactivation of viruses. The virus depletion preferably is effected by means of a filtration over nanofilters.

According to a further aspect, the present invention provides a preparation containing purified vWF having a high speficic activity, consisting particularly of high-molecular vWF multimers, obtainable from a vWF-containing solution by cation exchange chromatography. vWF having a high specific activity is enriched starting from a starting material containing, i.a., vWF of low purity and low specific activity, and accompanying proteins, in particular factor VIII or factor VIII complex containing low-molecular vWF multimers, are selectively separated. Thereby, in particular, a preparation containing purified vWF which particularly consists of high-molecular vWF multimers and which substantially is free from low-molecular vWF multimers and vWF degradation products, is recovered.

In particular, the preparation according to the invention has a specific platelet agglutinating activity of vWF of at least 65 U/mg protein, and a specific collagen-binding activity of at least 65 U/mg protein. Likewise, the preparation is characterized in that it is substantially free from factor VIII and has a factor VIII-content of <0.1%, based on the ratio of activity of vWF to factor VIII.

A further criterion for the purity and the low infectiousness of a product is also the absence of contaminating nucleic acids. The preparation according to the invention thus is substantially free from nucleic acids. "Substantially" here means that the content of nucleic acids is $\leq 0.7$, based on the ratio 260/280 nm. The nucleic acid may, however, also be quantitated according to a method, e.g. as has been described in EP 0 714 987 and EP 0 714 988.

When recovering and producing the preparation according to the invention with plasmatic vWF, yet also with recombinant vWF, as the starting material, optionally a virus depletion/or inactivation method is carried out, as has been described above, to remove infectious particles, a virus inactivation and/or a virus depletion in principle being possible before or after each purification step, starting from the starting material up to the pharmaceutical preparation produced. Thus the preparation according to the invention will be virus-safe in any event.

According to a preferred embodiment, the preparation according to the invention is present in storage-stable form. The preparation containing purified vWF with a high specific activity may be provided as a ready solution, lyophilisate, or in the deep-frozen state. On account of its purity, the preparation is particularly stable. It has been shown that the preparation according to the invention is stable for at least 6 months at −20° C., in solution for at least 4 weeks at 4° C., and as a lyophilisate for at least 1 year. It has been shown that within each respective period of time, the vWF activity is reduced by 10% at the most, and the multimer pattern of the vWF multimers does not show any substantial change.

The formulation of the preparation according to the invention may be effected in a known and common manner. The purified vWF contained in the preparation of the invention, is mixed with a buffer containing salts, such as NaCl, trisodium citrate dihydrate and/or $CaCl_2$, and amino acids, such as glycine and lysine, at a pH ranging from 6 to 8, and formulated into a pharmaceutical preparation.

The preparation may be used for producing a medicament for treating patients suffering from phenotypic hemophilia and vWD.

The invention will be explained in more detail and by way of the following examples and the drawing figures, however, it shall not be restricted to these exemplary embodiments.

Example 1 describes the purification of rvWF from culture supernatants of recombinant cells by means of cation exchange chromatography; Example 2 describes the purification of plasmatic vWF by means of cation exchange chromatography with a preceding anion exchange chromatography; Example 3 describes the purification of recombinant vWF by means of combined anion exchange/immune affinity and cation exchange chromatography.

EXAMPLE 1
Purification of vWF From Culture Supernatants of Recombinant Cells by Means of Cation Exchange Chromatography vWF was produced in recombinant CHO cells in a common culturing medium. After fermentation of the transformed cells, the culture medium was taken off, and cells and cell fragments were removed by centrifugation. Subsequently, the solution was clarified through filters having a pore size of 0.4 μm for removing low-molecular components, such as membrane fragments.

A chromatographic column (50 ml) was filled with a cation exchanger (Fractogel® EMD-SO3) and rinsed with buffer (30 mM glycine-NaCl-buffer). Subsequently, the cation exchange column was loaded with the cell-free culture supernatant, such proteins which do not bind to the exchanger being obtained in the effluent (Fraction 1). Bound, non-specific accompanying proteins were removed by rinsing the column with buffer containing 0.3 M NaCl (Fraction 2). Subsequently, bound vWF was desorbed from the exchanger by means of a buffer containing 0.5 M NaCl, and obtained in the eluate (Fraction 3).

Figure 1:
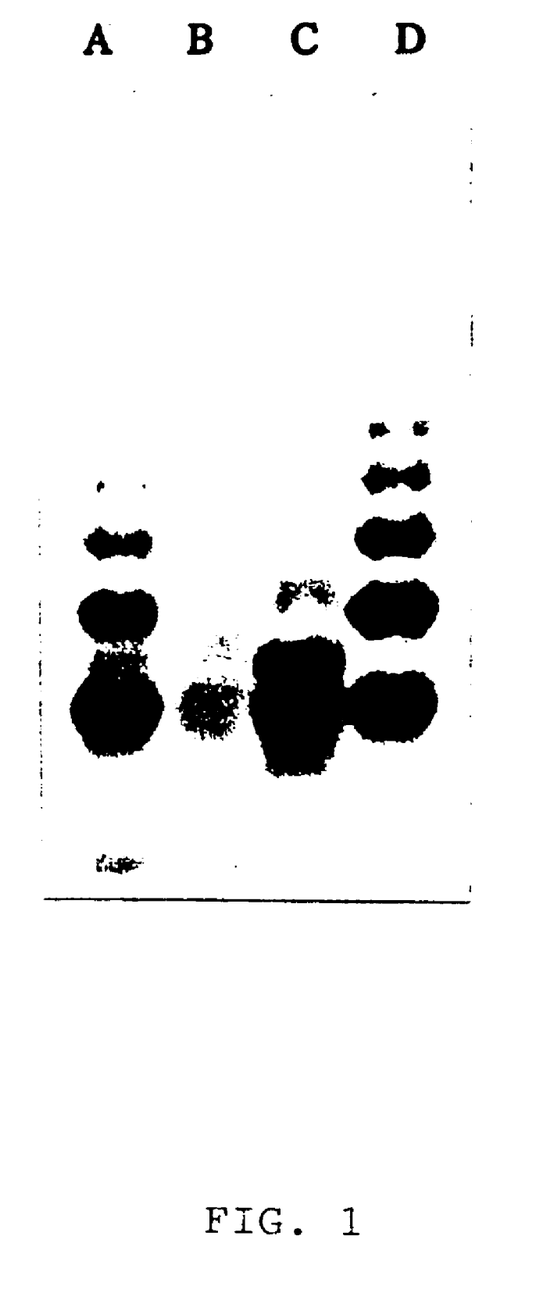
FIG. 1 shows a multimer analysis of rvWF before and after purification by means of cation exchange chromatography.

All the fractions were examined for their protein content, vWF antigen content (vWF:Ag), vWF activity (ristocetin-cofactor-activity, vWF:RistCoF), and subjected to a vWF multimer analysis. The protein concentration was determined by means of the Bradford method (M. Bradford (1976), Anal. Biochem., 72: 248–254). The vWF content was determined by means of a commercially available ELISA system (Asserachrom® vWF, Boehringer Mannheim). The ristocetin-cofactor activity was determined by means of a common test system (v-Willebrand-Reagenz®, Behringwerke). The results of the cation exchange chromatography are summarized in Table 1. FIG. 1 shows the vWF multimer analysis before and after purification via the cation exchanger.

From Table 1 it is apparent that the entire vWF present in the starting material and having ristocetin-cofactor activity is bound by the cation exchanger. By rinsing the cation exchange column with a buffer containing 0.3 M NaCl (Fraction 2), vWF having no measurable activity is removed. By elution with 0.5 M NaCl (Fraction 3), vWF having nearly all the ristocetin-cofactor activity is obtained. Furthermore, a pronounced depletion of DNA of the culture supernatant is attained: the absorption ratio 260 nm/280 nm drops from 1.2 to 0.7. From this single chromatographic step there results a purification factor of 10.

FIG. 1 shows the multimer analysis of vWF before and after purification by means of cation exchange chromatography. In FIG. 1, lane A shows non-purified rvWF, lane B shows vWF multimers of Fraction 1 in the effluent; lane C shows vWF multimers of Fraction 2 (0.3 M NaCl-eluate), and lane D shows those of Fraction 3 (0.5 M NaCl-eluate). From FIG. 1 it is apparent that by means of the cation exchange chromatography and a selective elution, a vWF particularly containing high-molecular multimer structures is obtained. Low-molecular vWF multimers and vWF degradation products, respectively, either are not bound to the cation exchanger (Fraction 1), or they are selectively separated by elution with 0.3 M NaCl (Fraction 2).

TABLE 1

Purification of recombinant vWF (rvWF) by means of cation exchange chromatography

| Sample | vWF:RistCoF (U/ml) | vWF:Ag (μg/ml) | UV absorption ratio 260 nm/280 nm |
| --- | --- | --- | --- |
| Non-purified vWF | 0.338 | 120.36 | 1.2 |
| Fraction 1 (Not bound) | 0 | 2.8 | 1.5 |
| Fraction 2 (Eluate 0.3 M NaCl) | 0 | 10.7 | 0.7 |
| Fraction 3 (Eluate 0.5 M NaCl) | 0.450 | 48.9 | 0.7 |

EXAMPLE 2
Purification of Plasmatic vWF Via Cation Exchanger with Preceding Purification Via Anion Exchanger A. Anion Exchange Chromatography Under Conditions Under Which vWF Binds to the Anion Exchanger, and Selective Elution of vWF Cryoprecipitate from human plasma was dissolved in a buffer of 7 mM Tris, 100 mM Na acetate, 100 mM lysine at pH 6.7. For a pre-treatment, $Al(OH)_3$ was stirred in. Subsequently, the precipitate was separated by centrifugation.

Cryoprecipitate pretreated in this manner was applied to an anion exchange column of Fractogel® EMD-TMAE. Weakly bound proteins were removed by rinsing the column with a 160 mM NaCl-containing buffer. By elution with 250 mM NaCl in the buffer, vWF primarily was eluted from the exchanger (Fraction 1). By elution with 400 mM NaCl, FVIII-complex was eluted subsequently (Fraction 2). Starting with cryoprecipitate, Fraction 1 contained 680 of the entire vWF activity, yet merely 10% of the entire FVIII activity. Residual vWF activity and 80% of the FVIII activity are contained in Fraction 2.

TABLE 2

Enrichment of vWF by means of anion exchange chromatography

| Sample | vWF:RistCoF-activity (U/ml) | FVIII:C activity (U/ml) |
|---|---|---|
| Cryoprecipitate | 13.5 | 13.6 |
| Fraction 1 (Eluate 250 mM NaCl) | 5.4 | 2.8 |
| Fraction 2 (Eluate 400 mM NaCl) | 4.5 | 11.8 |

The vWF-containing Fraction 1 was subsequently applied to a cation exchange column of Fractogel® EMD-SO3. Weakly bound proteins were removed by rinsing the column with 100 mM NaCl. Subsequently, it was eluted step-wise with 200 mM NaCl (Fraction 1), 300 mM NaCl (Fraction 2) and 400 mM NaCl (Fraction 3). More than 70% of the entire vWF activity were found in the 400 mM NaCl fraction. Not any FVIII:C activity was found. The results are summarized in Table 3.

TABLE 3

Step-wise elution of vWF fractions from the cation exchanger

| Sample | vWF:RistCoF-activity (U/ml) |
|---|---|
| vWF Fraction 1 (Tab. 2) | 5.4 |
| Fraction 1 (Eluate 200 mM NaCl) | 0 |
| Fraction 2 (Eluate 300 mM NaCl) | 0.2 |
| Fraction 3 (Eluate 400 mM NaCl) | 3.75 |

While the specific activity of vWF in the cryoprecipitate was 0.6 U/mg protein, it amounts to 65 U/ml in the 400 mM NaCl eluate following cation exchange chromatography. The specific collagen binding activity rose from 0.7 U/mg protein in the cryoprecipitate to 65 U/mg protein in the 400 mM NaCl eluate following cation exchange chromatography. Departing from the cryoprecipitate, the purity of vWF was increased 100-fold.

Figure 2:
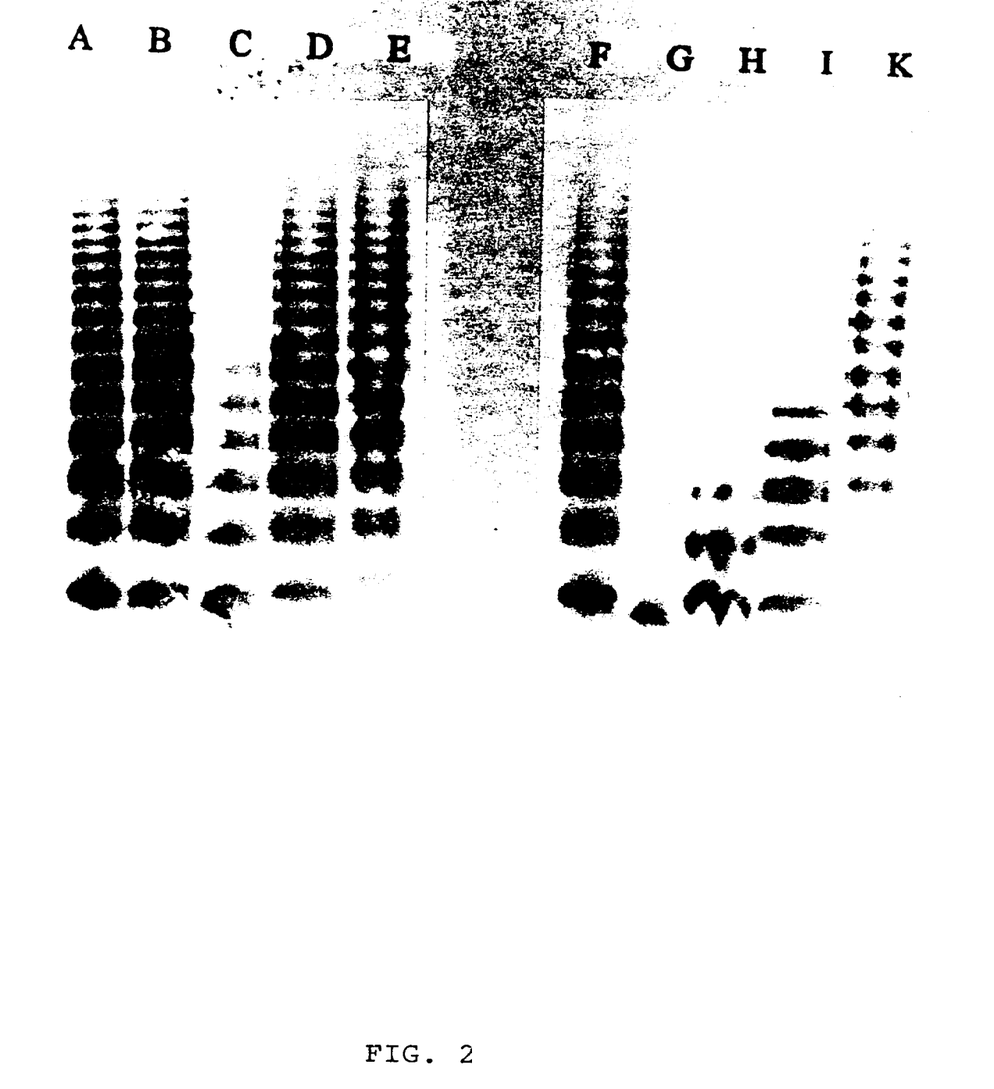
FIG. 2 shows a multimer analysis of vWF from cryoprecipitate, before and after purification by means of a combined anion/cation exchange chromatography under conditions under which vWP binds to the anion exchanger (Example 2A)

FIG. 2 shows the vWF multimer analysis during the combined anion/cation exchange chromatography. Lanes A to E show the purification via anion exchanger, and lanes F to K that via cation exchanger. FIG. 2, Lane A shows the vWF multimer pattern of vWF in the cryoprecipitate, Lane B that following filtration, Lane C that in the effluent, Lane D the 250 mM NaCl eluate (Fraction 1, Table 2), Lane E the 400 mM NaCl eluate (Fraction 2, Table 2), Lane F the 250 mM NaCl eluate (Fraction 1, Table 2) before the cation exchange chromatography, Lane G the effluent, Lane H the 200 mM NaCl eluate (Fraction 1, Table 3), Lane I the 300 mM NaCl eluate (Fraction 2, Table 3), and Lane K the 400 mM NaCl eluate (Fraction 3, Table 3). From Lanes H and I it can be seen that by elution with 200 mM NaCl or with 300 mM NaCl, respectively, merely low-molecular vWF multimers are detached from the cation exchanger. Elution of the cation exchanger with 400 mM NaCl, Lane K, gave vWF particularly containing high-molecular vWF multimers.

B. Anion Exchange Chromatography Under Conditions, Under Which vWF Does Not Bind to the Anion Exchanger and Remains in Solution Cryoprecipitate from human plasma was dissolved in a buffer of 7 mM Tris, 100 mM Na-acetate, 100 mM lysine, 120 mM NaCl, at pH 6.7. For a pre-treatment, $Al(OH)_3$ was stirred in. Subsequently, the precipitate was separated by centrifugation.

Cryoprecipitate pre-treated in this manner was applied to a column of Fractogel® EMD-TMAE. Non-bound proteins were obtained by rinsing the column with solution buffer (Fraction 1). This Fraction 1 contained 60% of the vWF activity and merely 10% of the FVIII activity. By elution of the column with 400 mM NaCl (Fraction 2), FVIII-complex was subsequently obtained.

TABLE 4

Enrichment of vWF by means of anion exchange chromatography

| Sample | vWF:RistCoF activity (U/ml) | FVIII:C activity (U/ml) |
|---|---|---|
| Cryoprecipitate | 12.5 | 12.2 |
| Fraction 1 (vWF not bound) | 3.5 | 0.7 |
| Fraction 2 (Eluate 400 mM NaCl) | 2.5 | 14.5 |

The vWF-containing Fraction 1 subsequently was applied to a cation exchange column (Fractogel® EMD-SO3). Weakly bound proteins were removed by rinsing the column with 100 mM NaCl. There followed a step-wise elution with 200 mM NaCl (Fraction 1), 300 mM NaCl (Fraction 2) and 400 mM NaCl (Fraction 3). More than 70% of the vWF activity were found in the 400 mM NaCl fraction. Not any factor VIII antigen and FVIII:C activity were found. The results are summarized in Table 5.

TABLE 5

Step-wise elution of vWF fractions from the cation exchanger

| Sample | vWF:RistCoF-activity (U/ml) |
|---|---|
| vWF (Fraction 1, Tab. 4) | 3.5 |
| Fraction 1 (Eluate 200 mM NaCl) | 0 |
| Fraction 2 (Eluate 300 mM NaCl) | 0.2 |
| Fraction 3 (Eluate 400 mM NaCl) | 3.75 |

While the specific activity of vWF in the cryoprecipitate was 0.6 U/mg protein, it amounts to 47 U/mg in the 400 mM NaCl eluate following cation exchange chromatography. The specific collagen binding activity rose from 0.7 U/mg protein in the cryoprecipitate to 51 U/mg protein in the 400 mM NaCl eluate following cation exchange chromatography. Departing from the cryoprecipitate, the purity of vWF was increased 80-fold.

Figure 3:
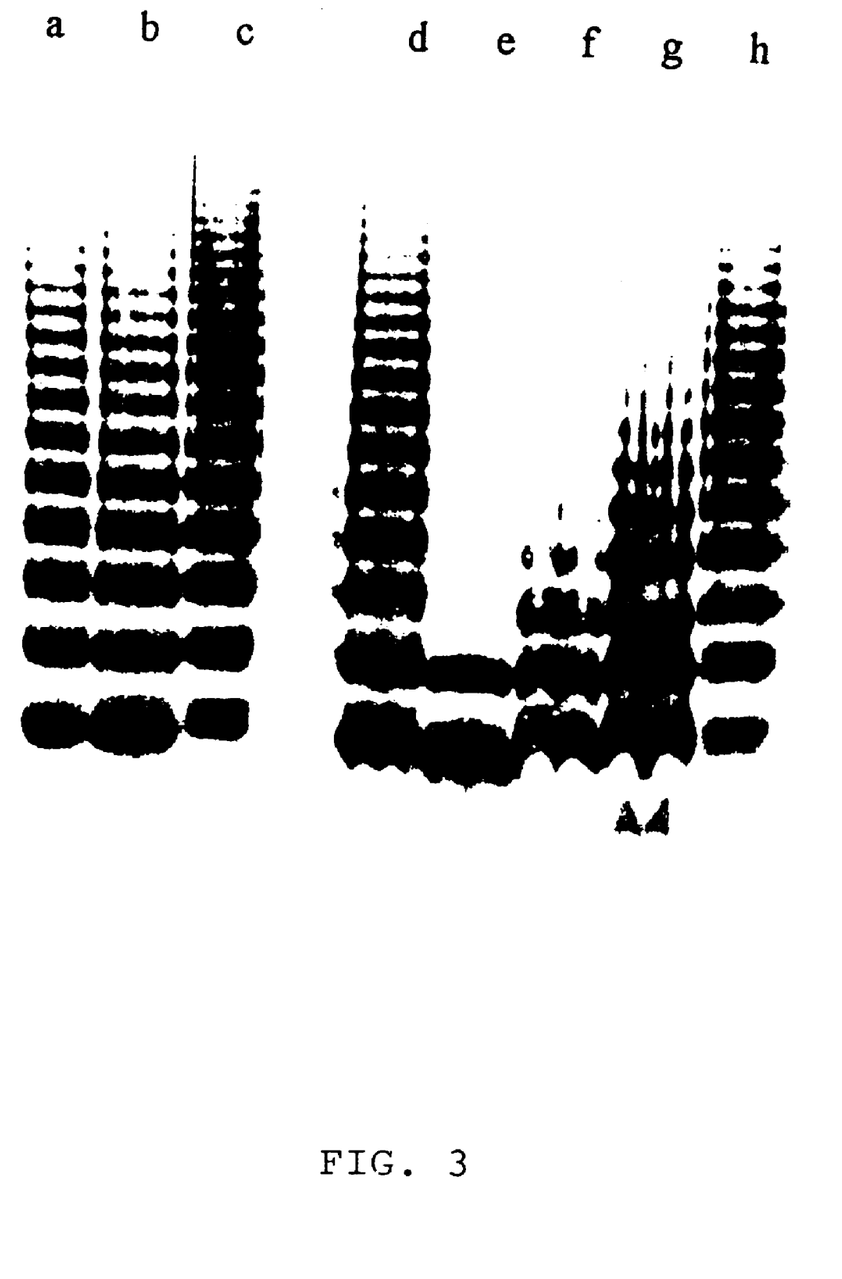
FIG. 3 shows a multimer analysis of vWF from cryoprecipitate before and after purification by means of combined anion/cation exchange chromatography under conditions, under which vWF does not bind to the anion exchanger (Example 2B).

FIG. 3 shows the vWF multimer analysis during the combined anion/cation exchange chromatography. Lanes a to c show the purification via anion exchanger, and Lanes d to h that via cation exchanger. FIG. 3, Lane a shows the vWF multimer pattern of vWF in the cryoprecipitate, Lane b in the effluent, Lane c the 400 mM NaCl eluate (Fraction 2, Table 4), Lane d the effluent (Fraction 1, Table 4) prior to cation exchange chromatography, Lane e the effluent via cation exchanger, Lane f the 200 mM NaCl eluate (Fraction 1, Table 5), Lane q the 300 mM NaCl eluate (Fraction 2, Table 5), and Lane h the 400 mM NaCl eluate (Fraction 3, Table 5). The vWF multimer structure of the vWF in the fractions obtained with 200 mM NaCl (Lane f) and 300 mM NaCl (Lane q), respectively, as well as 400 mM NaCl (Lane h) following cation exchange chromatography has been illustrated accordingly. The 400 mM NaCl eluate (Lane h) shows a high-molecular vWF multimer pattern and contains more than 70% of the vWF activity.

EXAMPLE 3
Purification of Recombinant vWF by Means of Combined Anion Exchange/immunoaffinity—and Cation Exchange Chromatography (at Present Considered by Applicant to be the Best Mode of Carrying out the Invention)

vWF was produced by recombinant CHO cells in a usual culturing medium. After fermentation of the transformed cells, the culture medium was taken off, cells and cell fragments were removed by centrifugation. Subsequently, the solution was filtered through filters having a pore size of 0.4 μm for removing low-molecular components, such as membrane fragments.

Anion Exchange Chromatography 1000 ml of cell-free culture supernatant were filtered at a flow rate of 0.7 cm/min over a column (7.1 cm$^2$×8 cm, filled with 57 ml of anion exchanger Fractogel® EMD-TMAE 650 M (Merck)). Before this, the gel had been equilibrated with 20 mM Tris-HCl buffer (pH 7.0). Subsequently, the column was washed with 20 mM Tris-HCl buffer (pH 7.0) which contained 0.1 M NaCl. Accompanying substances and vWF having a low RistCoF activity were removed by washing the column with 200 mM NaCl containing buffer. rvWF was then eluted from the carrier by means of 280 mM NaCl in 20 mM Tris-HCl buffer (pH 7.0).

Immunoaffinity Chromatography

The 280 mM NaCl-eluate from the anion exchanger step was loaded at a flow rate of 0.255 cm/min onto an immobilized antibody resin (column dimensions: 19.6 cm$^2$×5,6 cm; gel bed volume: 110 ml; resin matrix: Sepharose CL2B; antibody: Fab-fragments of the murine monoclonal antibody AvW8/2) that had been equilibrated with 20 mM Na-acetate, 300 mM NaCl (pH 7.0). This was followed by rinsing with 20 mM Na-acetate, 300 mM NaCl (pH 7.0) to which 0.5%. Tween 80 had been added. rvWF was eluted at pH 8.0 with 20 mM glycine buffer to which 10% sucrose had been added. After 80% of the column volume, the flow rate was reduced by the approximately 20-fold.

Cation Exchange Chromatography

A chromatographic column (7.1 cm$^2$×8 cm, filled with 57 ml Fractogel® EMD-SO3) was rinsed with buffer (30 mM glycine-NaCl-buffer; pH 5.0). Subsequently, the eluate from the immunoaffinity chromatography was filtered through the cation exchanger column. After washing the column again with 30 mM glycine-NaCl buffer, accompanying substances bound to the cation exchanger and vWF having a low specific activity were removed by rinsing the column with buffered 0.3 M NaCl solution. Subsequently, vWF was obtained in Fraction 3 from the exchanger column by elution with buffer containing 0.5 M NaCl.

After the individual chromatographic steps, the protein concentration, the content of rvWF antigen (vWF:Ag) and the ristocetin-cofactor activity (vWF:RistCoF) were determined.

It was found that rvWF is enriched by the factor 2.3 by. means of the anion exchange chromatography. In the subsequent immunoaffinity chromatography, a further enrichment by the factor 3.6 occurred. By means of the subsequent cation exchange chromatography, vWF could once more be enriched by a factor 5.2. Moreover, by this step the traces of murine antibody present in the eluate from the immunoaffinity column could practically completely be removed (<0.02 mg/1000 U vWF RistCoF activity). By a subsequent cation exchange chromatography, a separation of the low-molecular vWF multimers and an enrichment of vWF having high molecular multimer structures were effected, whereby the ratio of vWF:RistCoF to vWF:Ag activity is increased by the factor 4.

The results of the purification of rvWF in the different steps of this sequential purification procedure are illustrated in Table 6.

TABLE 6

Purification of recombinant vWF by means of combined anion exchange/immunoaffinity- and cation exchange chromatography

| Sample | Protein (mg/ml) | vWF:RistCoF (U/ml) | vWF:Ag (mg/ml) | vWF:RistCoF/Protein (U/mg) |
|---|---|---|---|---|
| Non-purified vWF | 0.626 | 1.013 | 0.116 | 1.62 |
| Eluate Anion exchanger | 0.684 | 2.588 | 0.322 | 3.78 |
| Eluate Immunoaffinity | 0.198 | 2.700 | 0.348 | 13.64 |
| Eluate Cation exchanger | 0.046 | 2.250 | 0.074 | 59.20 |

What is claimed is:

1. Delete "vWF" and Insert "von Willebrand factor (vWF)" in line 1 of the claim.

2. A method as set forth in claim 1, wherein said vWF is bound to said cation exchanger at a salt concentration of ≦250 mM, and wherein at least one vWF fraction containing high-molecular weight vWF multimers is eluted at a salt concentration of ≧300 mM.

3. A method as set forth in claim 2, wherein at least one vWF fraction containing said high-molecular weight vWF multimers is recovered by elution in a buffer having a pH ranging from 5.0 to 8.5.

4. A method as set forth in claim 3, wherein said pH of said buffer ranges between 6.0 and 8.0.

5. A method as set forth in claim 1, further comprising removing low-molecular weight vWF multimers, proteolytic vWF degradation products and other proteins at a salt concentration of between ≧250 mM and ≦300 mM.

6. A method as set forth in claim 1, wherein said cation exchanger is selected from the group consisting of a sulfopropyl group conjugated carrier and a carboxymethyl group conjugated carrier.

7. A method as set forth in claim 2, wherein at least one vWF-containing fraction containing high-molecular weight vWF multimers is recovered having a specific platelet agglutinating activity of at least 65 U/mg of protein and a specific collagen binding activity of at least 65 U/mg of protein.

8. A method as set forth in claim 2, wherein at least one vWF containing fraction recovered is substantially free from low-molecular weight vWF multimers, from vWF fragments with low specific vWF activity and from contaminating nucleic acids.

9. A method as set forth in claim 1, wherein said vWF-containing solution is selected from the group consisting of plasma, a plasma fraction, cryoprecipitate, a supernatant and an extract of a recombinant cell culture and an enriched protein solution.

10. A method as set forth in claim 9, wherein said enriched protein solution is obtained by a preceding purification step.

11. A method as set forth in claim 10, wherein said preceding purification step is a chromatographic method.

12. A method as set forth in claim 11, wherein said chromatographic method is selected from the group consisting of an anion exchange chromatography, an affinity chromatography and a combination thereof.

13. A method as set forth in claim 2, further comprising subjecting said at least one vWF-containing fraction recovered to at least one virus inactivation or a virus depletion step.

14. A preparation comprising purified von Willebrand factor (vWF) containing high-molecular weight vWF multimers, obtainable from a vWF-containing protein solution by cation exchange chromatography.

15. A preparation as set forth in claim 14, said preparation being substantially free from low-molecular weight vWF multimers, from inactive vWF degradation products and from contaminating nucleic acids.

16. A preparation as set forth in claim 15, wherein said vWF of said high-molecular weight vWF multimers has a specific platelet agglutinating activity of at least 65 U/mg of protein and a specific collagen binding activity of at least 65 U/mg of protein.

17. A preparation as set forth in claim 14, wherein said preparation is substantially free from factor VIII and has a factor VIII content of <0.1%, based on the ratio of activity of vWF to factor VIII:C.

18. A preparation as set forth in claim 14, wherein said preparation is virus-safe.

19. A preparation as set forth in claim 14, wherein said preparation is present in a storage-stable form.

20. A preparation as set forth in claim 14, wherein said preparation is formulated as a pharmaceutical preparation.

21. A method of treating a patient suffering from a disorder, selected from the group consisting of phenotypic hemophilia and von Willebrand Syndrome, by administering an effective dose of a von Willebrand factor (vWF)-containing preparation to said patient, said vWF-containing preparation comprising purified vWF containing high-molecular weight vWF multimers with a factor VHII content of 1% (total protein) or less, obtained from a vWF-containing protein solution by cation exchange chromatography.

22. The method of claim 1, wherein said vWF is bound to said cation exchanger at a salt concentration of $\leqq 250$ mm, and wherein the fractionated elution step comprises (i) eluting said cation exchanger with a salt concentration of between $\geqq 250$ mm and $\leqq 300$ mm; and (ii) eluting said cation exchanger with a salt concentration of $\geqq 300$ mm.

* * * * *

UNITED STATES PATENT AND TRADEMARK OFFICE
CERTIFICATE OF CORRECTION

PATENT NO. : 6,465,624 B1
DATED : October 15, 2002
INVENTOR(S) : Bernhard Fischer et al.

It is certified that error appears in the above-identified patent and that said Letters Patent is hereby corrected as shown below:

Title page, Item [54] and Column 1, lines 2-3,
In the Title the phrase "CATION EXCHANGER CHROMATOGRAPHY" should read -- CATION EXCHANGE CHROMATOGRAPHY --.

Column 1,
Lines 42-43, the phrase "a complex with factor VIII. which aids" should read -- a complex with factor VIII which aids --.

Column 4,
Line 1, "conqgntration" should read -- concentration --;
Line 8, the phrase "only such carrier-materials which" should read -- only such carrier materials which --.

Column 6,
Line 26, "speficic" should read -- specific --.

Column 9,
Line 4, the phrase "contained 680 of the" should read -- contained 68% of the --.

Column 11,
Line 4, the "Lane q" should read -- Lane g --;
Line 8, "(Lane q)" should read -- (Lane g) --;
Line 58, "19.6 cm$^2$x5,6" should read -- 19.6 cm$^2$ x 5.6 --.

Column 12,
Lines 16-17, the phrase "the factor 2.3 by. Means of the anion exchange chromatography." should read -- the factor 2.3 by means of the anion exchange chromatography. --.
Line 51, the phrase "Delete "vWF" and Insert "von Willebrand factor (vWF)" in line 1 of the claim" should be deleted and replaced with
-- A method of recovering von Willebrand factor (vWF), comprising:
    (a) providing a vWF-containing solution having a low salt concentration,
    (b) binding vWF at a low salt concentration to a cation-exchanger, and
    (c) subjecting said cation exchanger with said bound vWF to fractionated elution at increasing salt concentration until a sufficiently high salt concentration is reached so as to recover vWF of a high specific activity and a factor VIII content of 1% (total protein) or less. --.

UNITED STATES PATENT AND TRADEMARK OFFICE
CERTIFICATE OF CORRECTION

PATENT NO.   : 6,465,624 B1
DATED        : October 15, 2002
INVENTOR(S)  : Bernhard Fischer et al.

It is certified that error appears in the above-identified patent and that said Letters Patent is hereby corrected as shown below:

<u>Column 14,</u>
Line 25, the "factor VHII content" should read -- factor VIII content --.
Lines 30, 34 and 36, each occurrence of "mm" should read -- mM --

Signed and Sealed this

Twenty-second Day of April, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,465,624 B1
DATED         : October 15, 2002
INVENTOR(S)   : Fischer et al.

It is certified that error appears in the above-identified patent and that said Letters Patent is hereby corrected as shown below:

Column 13,
Line 35, after the word "multimers" the following text should be added
-- with a factor VIII content of 1% (total protein) or less --

Signed and Sealed this

Fifteenth Day of July, 2003

JAMES E. ROGAN
*Director of the United States Patent and Trademark Office*